(12) United States Patent
Kim et al.

(10) Patent No.: US 10,286,004 B2
(45) Date of Patent: May 14, 2019

(54) TARGETING-ENHANCED ANTICANCER NANOPARTICLES AND PREPARATION METHODS OF SAME

(71) Applicant: JINIS CO., LTD., Wanju-gun, Jeollabuk-do (KR)

(72) Inventors: Hyeon Jin Kim, Wanju-gun (KR); Seong Tshool Hong, Jeonju-si (KR); Hea Jong Chung, Jeonju-si (KR); Min Kyu Joo, Jeonju-si (KR); Hea Guk Cho, Gwangju (KR); Jinny Hong, Jeonju-si (KR)

(73) Assignee: JINIS CO., LTD., Wanju-gun (KR)

( * ) Notice: Subject to any disclaimer, the term of this patent is extended or adjusted under 35 U.S.C. 154(b) by 204 days.

(21) Appl. No.: 15/481,950

(22) Filed: Apr. 7, 2017

(65) Prior Publication Data
US 2017/0239369 A1 Aug. 24, 2017

Related U.S. Application Data

(62) Division of application No. 14/436,276, filed as application No. PCT/KR2013/004297 on May 15, 2013, now Pat. No. 9,662,401.

(30) Foreign Application Priority Data

May 2, 2013 (KR) .................. 10-2013-0049297

(51) Int. Cl.
| | | |
|---|---|---|
| *A61K 9/19* | (2006.01) | |
| *A61K 9/51* | (2006.01) | |
| *A61K 45/06* | (2006.01) | |
| *A61K 49/00* | (2006.01) | |
| *A61K 31/282* | (2006.01) | |
| *A61K 31/337* | (2006.01) | |
| *A61K 31/409* | (2006.01) | |
| *A61K 31/555* | (2006.01) | |
| *A61K 31/704* | (2006.01) | |
| *A61K 31/706* | (2006.01) | |
| *A61K 31/7068* | (2006.01) | |

(52) U.S. Cl.
CPC .............. *A61K 31/706* (2013.01); *A61K 9/19* (2013.01); *A61K 9/5123* (2013.01); *A61K 9/5169* (2013.01); *A61K 9/5192* (2013.01); *A61K 31/282* (2013.01); *A61K 31/337* (2013.01); *A61K 31/409* (2013.01); *A61K 31/555* (2013.01); *A61K 31/704* (2013.01); *A61K 31/7068* (2013.01); *A61K 45/06* (2013.01); *A61K 49/006* (2013.01); *A61K 49/0093* (2013.01)

(58) Field of Classification Search
None
See application file for complete search history.

(56) References Cited

U.S. PATENT DOCUMENTS

| | | | |
|---|---|---|---|
| 2007/0191473 A1 | 8/2007 | Desai et al. | |
| 2007/0231375 A1 | 10/2007 | Tsai et al. | |
| 2010/0209353 A1 | 8/2010 | Kwon et al. | |
| 2011/0142948 A1 | 6/2011 | Langer et al. | |

FOREIGN PATENT DOCUMENTS

| | | |
|---|---|---|
| JP | 2001-501931 A | 2/2001 |
| JP | 2013-513609 A | 4/2013 |
| KR | 10-0789008 B1 | 12/2007 |
| KR | 10-2010-0094664 A | 8/2010 |
| RU | 2452482 C2 | 6/2012 |
| WO | 2008109163 A1 | 9/2008 |
| WO | 2010150100 A1 | 12/2010 |

OTHER PUBLICATIONS

Ji-Eun Chang et al., "Liver Cancer Targeting of Doxorubicin with Reduced Distribution to the Heart Using Hematoporphyrin-Modified Albumin Nanoparticles in Rats," Pharm Res 2012, pp. 795-805, vol. 29.
International Searching Authority International Search Report for PCT/KR2013/004297 dated Feb. 10, 2014.
Ozgur, et al., "Synthesis and biological evaluation of radiolabeled photosensitizer linked bovine serum albumin nanoparticles as a tumor imaging agent", International Journal of Pharmaceutics, 2012, pp. 472-478 (8 pgs).
Japanese Patent Office, Communication dated Sep. 13, 2016 in counterpart Japanese application No. 2016-511662.
Canadian Patent Office: Communication dated Sep. 21, 2016, in counterpart application No. 2,911,157.
European Patent Office: Communication dated Jul. 8, 2016, in counterpart European Application No. 13883393.4.

(Continued)

*Primary Examiner* — Anand U Desai
(74) *Attorney, Agent, or Firm* — Sughrue Mion, PLLC

(57) ABSTRACT

Targeting-enhanced anticancer nanoparticles and preparation methods for the nanoparticles are provided. In particular, this invention provides targeting-enhanced anticancer nanoparticles comprising non-covalently bound anticancer drugs, serum albumins as the nanoparticle base material, and porphyrin compounds as tumor-targeting moieties. The targeting-enhanced anticancer nanoparticles described in the present invention are characterized by non-covalently bound constituents: anticancer drugs, serum albumin as the nanoparticle base material, and porphyrin compounds as tumor-targeting moieties, thus preventing common toxic side effects, enhancing the structural stability of nanoparticles, and enhancing tumor targeting by treatment with electromagnetic waves due to the activity of porphyrin, without structural and functional changes. Taken together, the present invention provides a chemotherapeutic method that maximizes drug delivery/tumor targeting and is expected to be a successful therapy for both early-stage and late-stage cancer.

7 Claims, 7 Drawing Sheets

(56) References Cited

OTHER PUBLICATIONS

Yang et al, "99mTc-hematoporphyrin linked albumin nanoparticles for lung cancer targeted photodynamic therapy and imaging", Journal of Materials Chemistry, Jan. 1, 2010 (Jan. 1, 2010) (5 pages total).

Zheng et al, "Single-step assembly of DOX/ICG loaded lipid-polymer nanoparticles for highly effective chemo-photothermal combination therapy", ACS Nano, pp. 2056-2067, Feb. 15, 2013 (Feb. 15, 2013).

Russian Federal Service for Intellectual Property, Communication dated Apr. 21, 2017, issued in corresponding Russian Application No. 2015150725/15.

State Intellectual Property Office of the P.R.C., Communication dated May 9, 2017, issued in corresponding Chinese Application No. 201380076274.2.

HMME, "Interaction of HMME, HB and THB with Plasma Serum and Serum Albumin", Chin J Laser Med Surg, vol. 17, No. 1, Feb. 2008 (10 pages total).

TARGETING-ENHANCED ANTICANCER NANOPARTICLES AND PREPARATION METHODS OF SAME

This application is a Divisional of Ser. No. 14/436,276 filed Apr. 16, 2015 in the U.S. Patent and Trademark Office, which is a National Stage of International Application No. PCT/KR2013/004297 filed May 15, 2013, claiming priority based on Korean Patent Application No. 10-2013-0049297 filed May 2, 2013, the contents of all of which are incorporated herein by reference in their entirety.

TECHNICAL FIELD

This invention provides targeting-enhanced anticancer nanoparticles and preparation methods for the same.

BACKGROUND ART

Cancer is the most devastating disease to modern society because there are no effective treatments that do not incur side effects. Although many treatments are available for cancer treatment, including surgery, radiation, phototherapy, and chemotherapy, used alone or in combination, it is still a challenging task to cure cancer.

Achieving clinical efficacy with the current chemotherapeutic drugs remains a significant challenge despite their strong efficacy in preclinical experiments; this difficulty is mostly due to their lack of tumor selectivity. The major issue is that only a fraction of anticancer drugs are actually delivered to the tumor tissues after the administration of chemotherapeutic drugs. The ineffective drug delivery of current chemotherapeutics results in a low intra-tumoral drug concentration, which decreases their chemotherapeutic efficacy. Furthermore, the administered anticancer drugs are mostly delivered to healthy tissues and thus cause various adverse side effects, such as bone marrow dysfunction, gastrointestinal disorders, alopecia, and immune dysfunction. Therefore, ineffective targeting of anticancer drugs eventually contributes to the development of multidrug resistance in tumor tissues and nonspecific toxicity in healthy tissues.

Therefore, to overcome the low efficacy and severe side effects of current therapeutics, it is essential to deliver more drug to tumor tissues and less drug to healthy tissues. Therefore, many researchers have studied ways to achieve selective targeted drug delivery to the tumor site.

One way to achieve selective drug targeting to solid tumors is to exploit the phenomenon of Extended Permeability and Retention, EPR, which is based on the abnormalities of the tumor vasculature (Maeda et al., J Controlled Release, 2000, 65: 271-284). Rapidly growing solid tumors feature widespread angiogenesis to meet the high metabolic needs of the tumor. The resulting blood vessels in angiogenesis-dependent solid tumors contain endothelial pores in the vascular membrane, which range in size from 10 nm to 1,000 nm. This leaky vasculature in tumor tissues enhances the vascular permeability of particles circulating in the blood. In addition, the impaired lymphatic system in tumor tissues enhances the retention of penetrated particles, particularly nano-sized macromolecules or nanoparticles. Thus, nanoparticles loaded with anticancer drugs can selectively extravasate from the systemic circulation to tumor tissues, resulting in preferential accumulation at much higher concentrations in tumor tissues than in healthy tissues or organs. Nanoparticle drugs have been demonstrated to selectively accumulate in tumors through the EPR effect, and this type of drug delivery is called passive targeting (Fang et al., Adv. Drug Delivery Rev., 2011, 63: 136-151; Danhier et al., J Controlled Release, 2010, 148: 135-146).

Abraxane® (Celgene Co.) is the first commercialized anticancer nanoparticle for metastatic breast cancer (U.S. Pat. Nos. 6,506,405, 6,537,579). Abraxane® is simply albumin-bound paclitaxel, i.e., the mitosis-inhibiting anticancer drug paclitaxel with albumin as the base material. This carrier does not contain an additional active targeting moiety, with the selective accumulation mostly depending on passive targeting. However, the tumor targeting efficiency of Abraxane® is enhanced less than 1.5-3 times compared with paclitaxel, due to its unstable nanostructure, which is not sufficient to significantly reduce side effects (Desai et al., Clin Cancer Res, 2006, 12: 1317-1324).

Ideally, nanoparticles should deliver cytotoxic drugs specifically to the targeted tumor tissues. To achieve efficient tumor targeting, nanoparticles need to exploit not only passive targeting by maintenance of a stable nanostructure but also active tumor-targeting by presenting tumor-targeting moieties on the nanoparticle surface. Many research teams have developed various nanoparticles with tumor targeting moieties (A. Swami et al., Multifunctional Nanoparticles for Drug Delivery Applications: Imaging, Targeting, and Delivery, Chapter 2. Nanoparticles for Targeted and Temporally Controlled Drug Delivery, p 9-p 29, Springer, 2012). However, these efforts have failed to achieve the commercialization of "targeting moiety nanoparticles," as described below.

Nanoparticles comprising only 2 components, a drug and a base material, can be relatively easily manufactured without covalent bonding by selecting a base material that is compatible with the intended anticancer drug. However, it is very difficult to prepare stable "targeting moiety nanoparticles" comprising 3 components, i.e., a drug, a base material, and a targeting moiety, without covalent bonding. To obtain a stable nanostructure, 3-component nanoparticles could be prepared by covalently bonding either the drug or the targeting moiety to the base material and then combining the third component with this complex. Unfortunately, the use of covalent bonds to prepare stable nanoparticles can cause the following problems. 1) Covalent bonding results in the formation of a new material that differs from the material prior to bonding. For instance, covalent bonding between hydrogen and oxygen forms the new molecule, water. Therefore, it is unavoidable for covalent bonding to form a new chemical entity, NCE. NCEs with new physicochemical properties could have unpredicted toxicities. 2) Covalent bonding of a drug changes its chemical structure, potentially negatively affecting its anticancer efficacy. 3) Covalent bonding of a targeting moiety changes its chemical structure, potentially negatively affecting its tumor targeting ability.

Another reason for the failure of "targeting moiety nanoparticles" is that attaching the targeting moiety to enhance tumor targeting can affect the structural stability of the nanoparticles and thus the capacity for passive targeting, preventing the tumor targeted delivery of the nanoparticles.

Another reason for the failure of "targeting moiety nanoparticles" is the technical difficulty involved in preparing a single nanoparticle made up of multiple heterogeneous components such as anticancer drugs, the base material, and targeting moieties, even with the incorporation of covalent bonding. Due to the technical challenges in the formation of a stable nanostructure with multiple components, many nanoparticles have been developed containing non-biological components such as metal (U.S. Pat. Nos. 7,364,919, 7,829,350, 8,236,284, 8,246,995, US Patent Pub. No. 20120052006, EP1671625, WO2002/098364, WO/2012/106713, WO/2012/075087). Unfortunately, nanoparticles containing non-biological components with anticancer efficacy in animal experiments failed to show good clinical efficacy but did exhibit serious toxicity.

The impact of binding targeting moieties to nanoparticles can be clearly observed in the case of "targeting moiety nanoparticles" in which porphyrin was covalently bound (conjugate) to serum albumin (Chang et al., Pharm. Res. 2012, 29:795-805). Serum albumin is the best base material for nanoparticles because of its harmlessness and its ability to non-covalently bind many different organic chemicals. Porphyrin, a precursor of heme, is a major targeting moiety that is able to accomplish tumor targeting for most cancer cells.

This nanoparticle with porphyrin covalently bound to albumin (conjugation) was expected to increase drug delivery efficiency. However, the anticancer efficacy was not significantly improved for the reasons mentioned above. In fact, the drug delivery efficiency of nanoparticles in which the targeting moiety porphyrin was conjugated to serum albumin was worse than that of nanoparticles in which only serum albumin was used for encapsulation (Chang et al., Pharm. Res. 2012, 29:795-805; Desai et al. Clin Cancer Res. 2006; 12:1317-1324).

As mentioned above, nanoparticles with active targeting moieties covalently bound at the surface are often thought to be superior to simple passively targeted nanoparticles, but none has reached commercialization due to the technical problems in preparing "targeting moiety nanoparticles".

The current commercially available nanoparticles are passively targeted nanoparticles in which the base material and anticancer drugs are non-covalently associated, including Abraxane, Doxil, Myocet, and Daunoxome. Therefore, there is an urgent need to develop structurally stable "targeting moiety nanoparticles" that consists of a non-toxic base material and a targeting moiety non-covalently bound at the surface.

Here, the present inventors tried to solve these problems and discovered a novel targeting-enhanced nanoparticle consisting of non-toxic serum albumin as the base material and porphyrin compound as the tumor targeting moiety. These nanoparticles were used to non-covalently encapsulate anticancer drugs, thereby avoiding structural changes in both the anticancer drugs and the tumor targeting moiety. The present inventors confirmed that 1) the drug maintains its anticancer efficacy without alteration; 2) active tumor targeting was enhanced by the preservation of the tumor targeting ability of the targeting moiety at the surface; 3) passive tumor targeting was enhanced by structural stability.

DISCLOSURE OF INVENTION

Technical Problem

Ideally, nanoparticles should deliver cytotoxic anticancer drugs precisely to the tumor tissues through the combined effects of active tumor targeting conferred by the active targeting moiety on the nanoparticle surface and of passive tumor targeting conferred by structural stability. However, various problems associated with previous nanoparticles have prevented the successful commercialization as described above.

The present invention attempts to solve these problems. One object of this invention is to provide a novel targeting-enhanced nanoparticle that is not only stable in its structure but also comprises a non-toxic base material and a tumor targeting moiety non-covalently attached at the surface. Another object of this invention is to provide a novel targeting-enhanced nanoparticle with significantly increased anticancer efficacy that is sufficient to cure late-stage cancers and results from the combination of passive and active targeting.

Technical Solution

To accomplish the said objects, the present invention provides novel targeting-enhanced nanoparticles comprising non-covalently bound human serum albumin as the base material, porphyrin compound as the tumor targeting moiety, and anticancer drugs.

The present invention also provides a preparation method comprising (a) a preparation step in which the anticancer drug solution is added to a solution of serum albumin; (b) a preparation step of nanoparticle aggregates of anticancer drugs and serum albumins by adding organic solvents drop wise to this mixture; (c) a manufacturing step for drug-albumin nanoparticles in which the spatial rearrangement of the components is induced by a temperature shift to yield nanoparticles with drugs in the core and serum albumin in the outer shell; (d) a manufacturing step for targeting-enhanced nanoparticles comprising non-covalently bound anticancer drugs, serum albumin, and porphyrin compounds in which drug-albumin nanoparticles are coated with porphyrin compounds; (e) an additional manufacturing step for the targeting-enhanced nanoparticles consisting of filtration, centrifugation, and recovery of the sedimented nanoparticles; and (f) a preparation step for the targeting-enhanced nanoparticles in which they are freeze-dried.

The present invention also provides targeting-enhanced nanoparticles prepared by said preparation method.

The present invention further provides a pharmaceutical composition comprising said targeting-enhanced anticancer nanoparticles.

Advantageous Effects

The targeting-enhanced anticancer nanoparticles from the present invention are characterized by the non-covalent encapsulation of anticancer drugs with non-toxic serum albumins and surface coating with porphyrin compounds as targeting moieties, without the formation of NCEs and structural alterations.

Therefore, the present invention provides a targeting-enhanced anticancer nanoparticle with maximized tumor targeting and drug delivery by 1) preventing toxicity originating from common nanoparticle components and composition of nanoparticles; 2) preventing a decrease in anticancer drug efficacy by maintaining the properties of anticancer drugs without structural alteration; 3) maintaining the active tumor targeting properties of porphyrin compounds non-covalently bound to the nanoparticles; and 4) maintaining the passive tumor targeting properties due to the structural stability.

BEST MODES

Figure 1A:
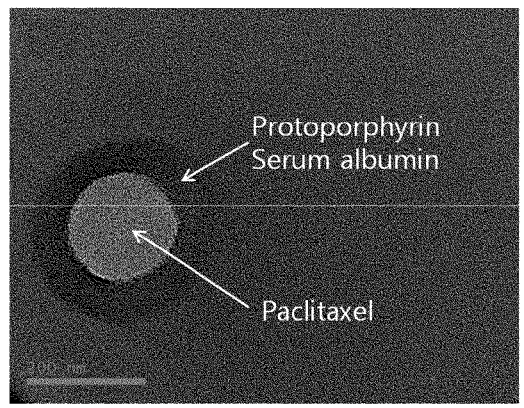
FIGS. 1A and 1B are Transmission Electron Microscopy (TEM) images of the targeting-enhanced anticancer nanoparticles prepared by the method in Example 1 (FIG. 1A: A targeting-enhanced nanoparticle of paclitaxel, FIG. 1B: A targeting-enhanced nanoparticle of cedrol).

Though nanoparticles with active targeting moieties are thought to be highly promising, none has successfully reached commercialization due to the technical problems involved in the preparation of stable "targeting moiety nanoparticles" without causing serious side effects.

Based on the understanding that covalent bonds could negatively affect the efficacy and toxicity of "targeting moiety nanoparticles", we attempted to confirm that a preparation of "targeting moiety nanoparticles" without using covalent bonds could enhance the efficacy of drug delivery to the tumor tissues.

Therefore, the present invention provides "targeting-enhanced nanoparticles" by 1) preparing serum albumin as the base material and porphyrin compounds as targeting moieties; 2) attaching targeting moieties with tumor targeting functionality to the nanoparticle shell; 3) encapsulating anticancer drugs in the nanoparticle cores, surrounded by the shell; and 4) preparing nanoparticles comprising drugs, serum albumin and porphyrin compounds non-covalently without altering the physiochemical and structural properties of the components. Thus, present inventors confirmed the 1) anticancer efficacy of encapsulated drugs; 2) maintenance of the active tumor targeting properties of porphyrin compounds non-covalently bound to the surface of nanoparticles; 3) maintenance of the passive tumor targeting properties due to structural stability; and 4) additional amplification of tumor targeting and drug delivery by irradiation with electromagnetic waves after the administration of prepared "targeting-enhanced nanoparticles".

In Example 1, the targeting-enhanced nanoparticles of paclitaxel were prepared by mixing paclitaxel solution and human serum albumin solution, adding organic solvents drop wise to induce the aggregation of paclitaxel and serum albumin, inducing spatial rearrangement through a temperature shift for (core drug)-(albumin shell) nanoparticles, coating with porphyrin compounds, and freeze-drying to obtain targeting-enhanced nanoparticles comprising non-covalently bound anticancer drugs, serum albumin, and porphyrin compounds. The present inventors confirmed that structure of non-covalently prepared targeting-enhanced nanoparticles were found to be stable, with the result that tumor targeting was sufficiently enhanced to exhibit excellent anticancer efficacies in both early stage and late-stage cancer.

Therefore, in the first aspect, the present invention relates to the targeting-enhanced nanoparticles, non-covalently comprising anticancer drugs, serum albumin as the base material, and porphyrin compounds as active tumor targeting moieties.

Said targeting-enhanced nanoparticles contain anticancer drugs in the nanoparticle core and the serum albumin-porphyrin complex at the outer nanoparticle shell.

Said targeting-enhanced nanoparticles encapsulate anticancer drugs in the nanoparticle core without covalent bonding to the shell components such as the serum albumin and porphyrin compounds, maintaining the structure and function of the anticancer drugs.

Said targeting-enhanced nanoparticles are characterized by porphyrin targeting moieties present in the nanoparticle shell, non-covalently bound to maintain the structure and function of tumor targeting moieties.

Said targeting-enhanced nanoparticles are characterized by serum albumin as the base material in the nanoparticle shell, thereby conferring passive targeting by stabilizing the nanoparticles and enhancing EPR. Said serum albumins can be any serum albumins but preferably serum albumins derived from mammals.

Said serum albumins are characterized by solubility in water without aggregate formation, but the addition of porphyrin compounds in organic solvent to the aqueous serum albumin solution induces non-covalent association between the serum albumin and porphyrin compounds.

In a preferred embodiment of the invention, said anticancer drugs can be any pharmaceutical materials with therapeutic efficacy against cancerous cells and/or tissues that belong to groups that include, but are not limited to, taxenes, antimetabolite agents, platinum agents, alkylating agents, anthracycline antibiotics, vinca alkaloids, proteasome inhibitors, macrolides, topoisomerase inhibitors, and others.

Said anticancer drugs include, but are not limited to, doxorubicin, daunorubicin, valrubicin, epirubicin, idarubicin, paclitaxel, docetaxel, cisplatin, carboplatin, oxaliplatin, camptothecin, vincristine, vinblastine, 5-fluorouracil (5-FU), mitomycin, cyclophosphamide, methotrexate, mitoxantron, topotecan, capecitabine, doxifluridine, irinotecan, tegafur, chlorambucil, belotecan, anasterozole, tamoxifen, gleevec, floxuridine, leuprolide, flutamide, zoledronate, streptozocin, vinorelbine, hydroxyurea, retinoic acid, meclorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, and any combinations of the above or derivatives thereof.

In a preferred embodiment of the invention, said porphyrin compounds exhibit an active targeting function to tumor tissues through the presence of over-expressed receptors in cancer cells. Said photosensitizers include, but are not limited to, protoporphyrin, heme, hemin, zinc protoporphyrin, magnesium protoporphyrin, hematoporphyrin, benzoporphyrin, metalloporphyrin, 5-aminolevulinic acid, texaphyrins, chlorins, purpurins, bacteriochlorins, pthalocyanine, napthalocyanine, and any combinations of the above or derivatives thereof.

Said porphyrin compounds exhibit an active tumor tissue targeting function through binding to receptors over-expressed in cancer cells.

Said porphyrin compounds confer an active targeting function to nanoparticles because tumors prefer these compounds under active angiogenesis. Selective binding to over-expressed receptors in tumor tissues, followed by internalization into the cancer cells through receptor-mediated endocytosis, results in selective accumulation in the tumor tissue.

Said porphyrin compounds also confer a passive targeting function to nanoparticles because the porphyrin compounds non-covalently form a shell complex with serum albumin, thereby stabilizing the nanoparticles and enhancing the enhanced permeability and retention (EPR) phenomena.

Said targeting-enhanced nanoparticles in this invention exhibit improved tumor targeting due to the enhanced passive targeting resulting from the stability of these nanostructures, enhanced active targeting through active targeting moieties present in the nanostructure shell, and further amplification of tumor targeting and EPR by electromagnetic radiation.

In another aspect, the present invention relates to a preparation method of non-covalently bound targeting-enhanced nanoparticles comprising (a) a preparation step of a mixture solution in which the anticancer drug solution is added to serum albumin solution; (b) a nanoparticle aggregate preparation step in which anticancer drugs and serum albumins aggregate upon the addition of organic solvents drop wise to the said mixture; (c) a manufacturing step in which drug-albumin nanoparticles are prepared with drugs in the core and serum albumin as the outer shell by inducing the spatial rearrangement of components through a temperature shift in these nanoparticle solutions with non-covalent aggregates of drugs and albumins; (d) a manufacturing step to prepare targeting-enhanced nanoparticles comprising non-covalently bound anticancer drugs, serum albumin, and porphyrin compounds by coating drug-albumin nanoparticles with porphyrin compounds; (e) a manufacturing step in which the targeting-enhanced nanoparticles were filtered and centrifuged and then the sedimented nanoparticles were recovered; and (f) a preparation step in which the targeting-enhanced nanoparticle powder was prepared by freeze-drying.

In a preferred embodiment of the invention, said targeting-enhanced anticancer nanoparticles are prepared by mixing constituents so that the ratio of said albumins, anticancer drugs, and porphyrin compounds is 100: (10-300): (0.01-10) by weight.

Desirable nanoparticle sizes may not result in targeting-enhanced nanoparticles for mixture ratios outside of said range.

In a preferred embodiment of the invention, said albumin solution, porphyrin solution, and anticancer drug solution can be prepared using organic and/or inorganic solvents that include, but are not limited to, saline, water, ethanol, methanol, acetone, dichloromethane, and others. Preferably, the concentration can be, but is not limited to, the range of 0.1~100 mg/ml.

In a preferred embodiment of the invention, the mixture of serum albumin and drugs can be prepared at pH 5~9 at various temperatures depending on the nature of the drugs, with room temperature preferred for hydrophobic drugs and cool temperatures ranging from 0° C. to room temperature preferred for hydrophilic drugs. Desirable nanoparticle sizes may not be achieved for targeting-enhanced nanoparticles prepared at conditions outside said range.

In a preferred embodiment of the invention, the aggregates of anticancer drugs and serum albumins can be prepared by adding organic solvents that include, but are not limited to, ethanol, acetone, acetonitrile, and others. Preferably, the addition speed can be, but is not limited to, the range of 0.1~0.9 ml/min for 6~13 minutes.

In a preferred embodiment of the invention, spatial rearrangement among constituents in the aggregates of anticancer drugs and serum albumins is induced by temperature shifts, with heating for hydrophobic drugs and cooling for hydrophilic drugs.

In some embodiments of the invention, for instance with paclitaxel as an anticancer drug, said spatial rearrangement among constituents in the aggregates of anticancer drugs and serum albumins is induced by heating at 40° C.~60° C. to evaporate organic solvents, resulting in core-shell nanoparticles in which hydrophobic paclitaxel molecules aggregated in the inner core and serum albumins were present on the outside shell.

In some embodiments of the invention with doxorubicin as an anticancer drug, for instance, said spatial rearrangement is induced by cooling at −10° C.~−70° C., resulting in core-shell nanoparticles in which the hydrophilic doxorubicin aggregated in the inner core and serum albumin formed the outer shell.

Desirable core drug and albumin shell structures may not be achieved at heating temperatures below 40° C. due to the poor evaporation of the organic solvent and above 60° C. due to the denaturation of constituents. The desired spatial rearrangement may not occur at cooling temperatures above −10° C. or below −70° C.

In a preferred embodiment of the invention, said targeting-enhanced anticancer nanoparticles comprising non-covalently bound anticancer drugs, serum albumin, and porphyrin compounds are prepared by coating drug-albumin nanoparticles with porphyrin compounds at room temperature.

In a preferred embodiment of the invention, said targeting-enhanced anticancer nanoparticles are prepared through filtration, centrifugation, and recovery of the sedimented nanoparticles.

In a preferred embodiment of the invention, said targeting-enhanced anticancer nanoparticles are prepared by an additional step of ultrasound treatment before the filtration step to separate randomly aggregated nanoparticles and to control the nanoparticle size.

Said ultrasound treatment results in grinding effects and the dispersion of the nanoparticles. Preferably, said ultrasound treatment is carried out at 10~30 KHz at 30-second intervals for more than 2 minutes, followed by filtration with a 0.45 μm filter and the recovery of nanoparticles by centrifugation.

Preferably, said targeting-enhanced anticancer nanoparticles have diameters in the range of 10~4,000 nm, preferably in the range of 50~400 nm.

In a preferred embodiment of the invention, said targeting-enhanced anticancer nanoparticles are freeze-dried. Removal of water by freeze-drying promotes the formation of polymer between porphyrin compounds and serum albumin, promoting the stabilization of this non-covalent structure.

Before use, freeze-dried targeting-enhanced anticancer nanoparticles are solubilized using 0.9% saline solution, for instance.

In another aspect, the present invention relates to targeting-enhanced nanoparticles that are prepared by said method, comprising non-covalently bound anticancer drugs, serum albumin as the nanoparticle base material, and porphyrin compounds as active tumor targeting moieties.

In another aspect, the present invention relates to a pharmaceutical composition comprising targeting-enhanced anticancer nanoparticles.

The dosage and administration method of said targeting-enhanced anticancer nanoparticles or said pharmaceutical composition can be easily determined by clinical references and knowledge in the field regarding the anticancer drugs that constitute said targeting-enhanced anticancer nanoparticles.

In a preferred embodiment of the invention, said targeting-enhanced anticancer nanoparticles or said pharmaceutical compositions provide a cancer therapy that includes, but is not limited to, irradiation of electromagnetic waves involving the activation of porphyrin compounds.

Said electromagnetic waves occur with changes in the electric field and magnetic field over time including, but not limited to, gamma-rays, X-rays, infrared, visible light, ultraviolet, microwaves, radio frequencies. Preferably, LED lights can be used to apply visible light electromagnetic treatment.

The present invention provides targeting-enhanced anticancer nanoparticles in which non-covalently bound porphyrin compounds maintain their structure and function, enabling the amplification of tumor targeting and EPR by activation with irradiation at the appropriate electromagnetic wavelengths.

In a preferred embodiment of the invention, intravenous administration of targeting-enhanced anticancer nanoparticles results in preferential delivery of nanoparticles to the tumor site and the activation of porphyrin compounds by electromagnetic waves generates cytotoxic ROS at the tumor site, in turn enhancing vascular damage, vascular permeability, tumor cytotoxicity, EPR, intra-tumoral drug concentration, tumor targeting, and cancer cell death, eventually curing the cancer through exponentially enhanced tumor targeting.

After the administration of said targeting-enhanced anticancer nanoparticles or said pharmaceutical compositions, patients can be subjected to irradiation with electromagnetic waves, improving anticancer efficacy due to the exponentially enhanced tumor targeting.

Said treatments involving irradiation with electromagnetic waves in association with intravenous administration of targeting-enhanced anticancer nanoparticles or said pharmaceutical composition can be easily determined by clinical references and knowledge in the field.

EXAMPLES

The present invention may be better understood with reference to the accompanying examples that are intended for purposes of illustration only and should not be construed to limit the scope of the invention, as defined by the claims appended hereto.

Example 1: Preparation of Targeting-Enhanced Nanoparticles Encapsulating Hydrophobic Anticancer Drugs The targeting-enhanced nanoparticles comprising non-covalently bound HSA, porphyrin, and hydrophobic anticancer drugs were prepared by the method described below.

88 mg of HSA (Lee Biosolutions, USA) was dissolved in 10 mL of 10 mM NaCl by stirring slowly, and its pH was adjusted to 8.0-8.5 by adding 1N NaOH. Then, 10 mg of paclitaxel (LC Laboratories, USA) was partially dissolved in 1 mL of ethanol and added to the HSA solution at the rate of 0.5 mL/min while being actively stirred.

The mixed solution of HSA and paclitaxel was stirred for more than 4 hours at room temperature, followed by adding ethanol at 0.5 mL/min to obtain the nanoparticle solution. The addition of approximately 4 mL of ethanol resulted in the formation of paclitaxel-HSA aggregates, turning the clear solution into a non-transparent milky color.

The ethanol in the paclitaxel-HSA aggregate solution was removed by heating at 45° C. using a rotary evaporator, which resulted in core-shell nanoparticles in which the hydrophobic paclitaxel was aggregated in the inner core and serum albumin formed the outer shell.

To the paclitaxel-HSA solution, 1 mg of protoporphyrin IX (SIGMA-ALDRICH) dissolved in 0.5 mL of ethanol was added to coat the paclitaxel-HSA nanoparticles, resulting in targeting-enhanced nanoparticles comprising non-covalently bound HSA, porphyrin, and paclitaxel.

To further optimize the size, the nanoparticle solution was treated with ultrasound at 20 KHz for 2 minutes at 30-second intervals. The obtained nanoparticle solution was filtered through a 0.45 μm filter and then centrifuged for 20 min at 50,000×g.

The sedimented nanoparticles were solubilized in 1 mL of 10 mM NaCl, freeze-dried, and stored for long-term use. The prepared nanoparticle powder can be used after solubilization in 0.9% saline solution, if necessary. The targeting-enhanced nanoparticles containing paclitaxel were reddish brown in color.

The prepared nanoparticles were observed by atomic force microscopy, AFM, and transmission electron microscopy, TEM, and their diameters were determined.

Figure 1B:
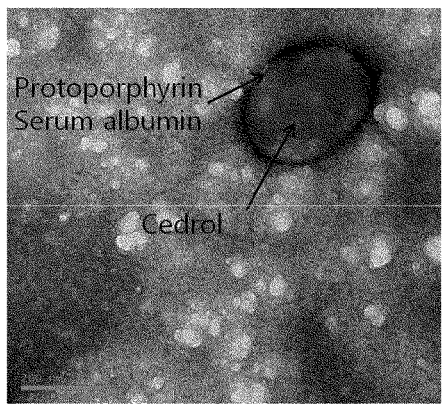
Figure 2A:
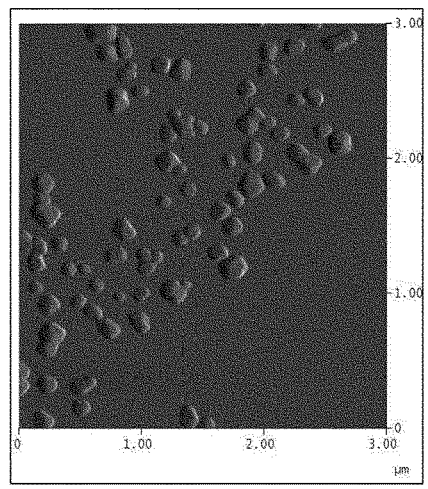
FIGS. 2A and 2B are images of the targeting-enhanced nanoparticles of paclitaxel prepared by the method in Example 1 (FIG. 2A: AFM image, FIG. 2B: TEM image).
Figure 2B:
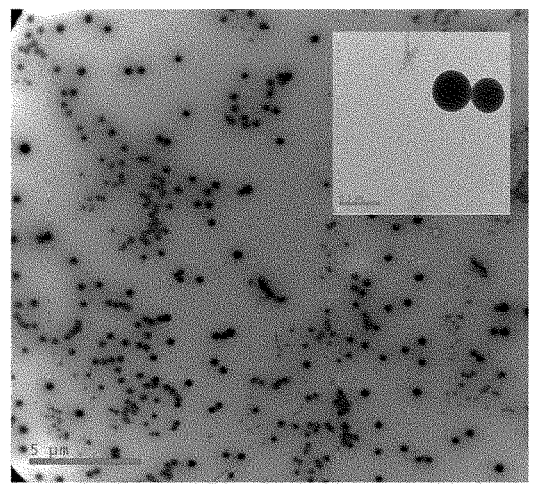

The targeting-enhanced anticancer nanoparticles can be prepared with other hydrophobic drugs by the same method illustrated above for paclitaxel. In this Example, targeting-enhanced nanoparticles were prepared with cedrol by the same method described above. The average diameters of the prepared targeting-enhanced nanoparticles are shown in Table 1. FIGS. 1A and 1B present the TEM images of the targeting-enhanced nanoparticles and FIGS. 2A and 2B present the AFM and TEM images of the targeting-enhanced nanoparticles containing paclitaxel prepared by the method in Example 1.

TABLE 1

| nanoparticles | average diameter (nm) |
|---|---|
| targeting-enhanced nanoparticles with paclitaxel | ~220 |
| targeting-enhanced nanoparticles with cedrol | ~210 |

Example 2: Preparation of Targeting-Enhanced Nanoparticles Encapsulating Hydrophilic Anticancer Drugs Targeting-enhanced nanoparticles comprising non-covalently bound HSA, porphyrin, and hydrophilic anticancer drugs were prepared using the method described below.

88 mg of HSA (Lee Biosolutions, USA) and 20 mg of doxorubicin (Chemieliva, China) was dissolved in 10 mL of 10 mM NaCl by stirring slowly, and the pH was adjusted to 8.0-8.5 by 1N NaOH.

Then, the mixed solution of HSA and doxorubicin was cooled to 4° C. for 1 hour with stirring, and ethanol was added at 0.5 mL/min with active stirring to obtain the nanoparticle solution. The addition of approximately 10 mL of ethanol resulted in the formation of doxorubicin-HSA aggregates, turning the clear solution into a non-transparent milky color.

The aggregate solution of doxorubicin-HSA was frozen to −20° C., kept on ice for more than 2 hours, and thawed slowly, resulting in core-shell nanoparticles in which hydrophilic doxorubicin was aggregated in the inner core and serum albumin formed the outer shell.

To the doxorubicin-HSA solution, 1 mg of protoporphyrin IX (SIGMA-ALDRICH) dissolved in 0.5 mL of ethanol was added to coat the doxorubicin-HSA nanoparticles, resulting in targeting-enhanced nanoparticles comprising non-covalently bound HSA, porphyrin, and doxorubicin.

To further optimize the size, the nanoparticle solution was treated with ultrasound at 20 KHz for 2 minutes at 30-second intervals. The obtained nanoparticle solution was filtered through a 0.45 μm filter and then centrifuged for 20 min at 50,000×g.

The sedimented nanoparticles were solubilized in 1 mL of 10 mM NaCl, freeze-dried, and stored for long-term use. The prepared nanoparticle powder can be used after solubilization in 0.9% saline solution, if necessary. The targeting-enhanced nanoparticles containing doxorubicin were reddish brown in color.

The prepared nanoparticles were observed by AFM and TEM and their diameters were determined.

Figure 3A:
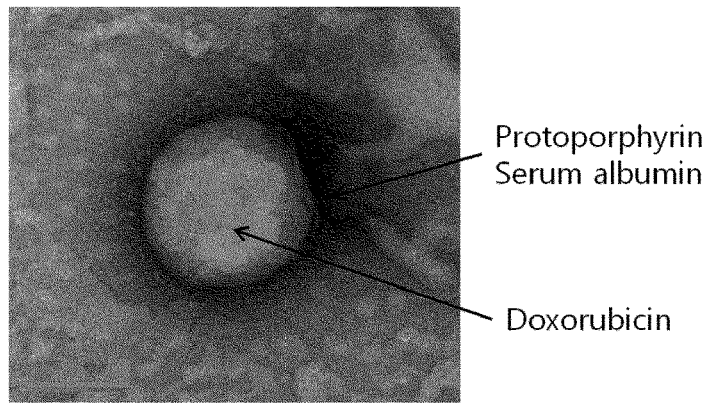
FIGS. 3A, 3B and 3C are the Transmission Electron Microscopy (TEM) images of the targeting-enhanced anticancer nanoparticles prepared by the method in Example 2 (FIG. 3A: A targeting-enhanced nanoparticle of doxorubicin, FIG. 3B: A targeting-enhanced nanoparticle of oxaliplatin, FIG. 3C: A targeting-enhanced nanoparticle of gemcitabine).
Figure 3B:
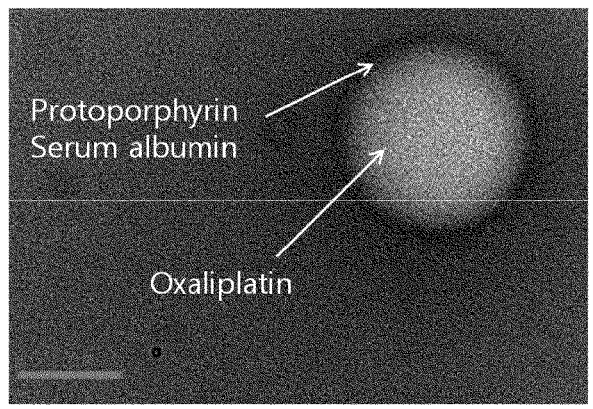
Figure 3C:
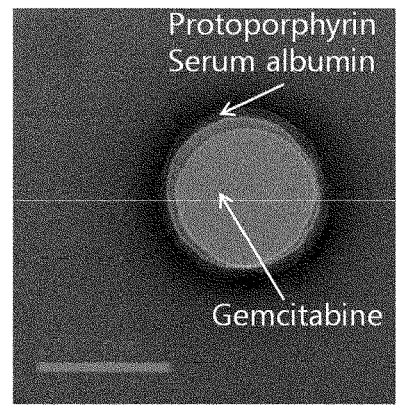
Figure 4A:
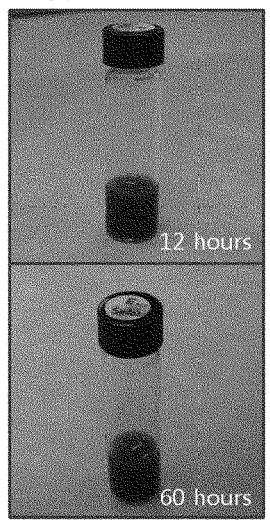
FIGS. 4A through 4D are images of solutions of targeting-enhanced anticancer nanoparticles prepared by the method in Example 1 and Example 2 to confirm the time course, tested 12 hours and 60 hours after solubilization (FIG. 4A: A targeting-enhanced nanoparticle solution of paclitaxel, FIG. 4B: A targeting-enhanced nanoparticle solution of doxorubicin, FIG. 4C: A targeting-enhanced nanoparticle solution of oxaliplatin, FIG. 4D: A targeting-enhanced nanoparticle solution of gemcitabine).
Figure 4B:
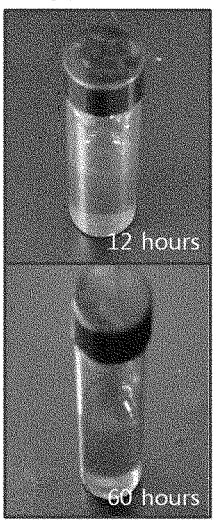
Figure 4C:
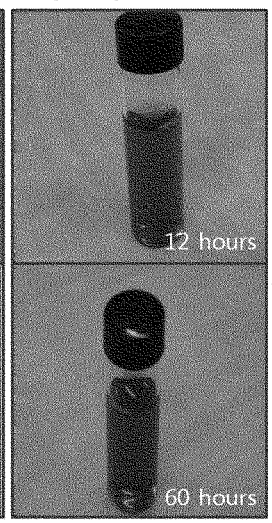
Figure 4D:
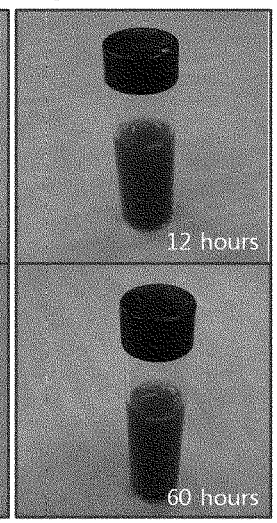

In this Example, targeting-enhanced anticancer nanoparticles were prepared with other hydrophilic drugs, including oxaliplatin (Sigma-Aldrich) and gemcitabine by the same method as described above for doxorubicin. Table 2 presents the average diameters of these targeting-enhanced nanoparticles. FIGS. 3A, 3B and 3C present the TEM images of the targeting-enhanced nanoparticles of the hydrophilic drugs doxorubicin, oxaliplatin, and gemcitabine.

TABLE 2

| nanoparticles | average diameter (nm) |
|---|---|
| targeting-enhanced nanoparticles with doxorubicin | ~180 |
| targeting-enhanced nanoparticles with oxaliplatin | ~220 |

TABLE 2-continued

| nanoparticles | average diameter (nm) |
|---|---|
| targeting-enhanced nanoparticles with gemcitabine | ~180 |

Experiment 1: Structural Stability of Targeting-Enhanced Nanoparticles

To confirm the structural stability of the targeting-enhanced nanoparticles prepared in Examples 1 and 2, their structures in aqueous solution were examined. The freeze-dried powders of the targeting-enhanced nanoparticles were solubilized in saline solution and kept for 12 hours and 60 hours at room temperature. FIGS. 4A through 4D present photographic images of solutions of the targeting-enhanced nanoparticle solutions of the anticancer drugs paclitaxel(A), doxorubicin(B), oxaliplatin(C), and gemcitabine(D), indicating that they remained stable for more than 60 hours after solubilization.

Experiment 2: Tumor Targeting Efficacy of Targeting-Enhanced Nanoparticles

To evaluate the tumor-targeting characteristics of the targeting-enhanced nanoparticles formulated in the Examples 1 and 2, the nanoparticles were injected into mice containing human breast xenograft tumors, and the distribution of radioactivity between tumor tissues and healthy tissues was analyzed.

The breast cancer cell line MDA-MB-231 (KCLB®, Korean Cell Line Bank) was prepared as a cell suspension, and $5\times10^6$ cells were injected subcutaneously into 6- to 8-week-old female athymic nude mice (Damool Science, Korea) in a specific pathogen-free environment. When the tumors reached a size of ~100 mm$^3$, mice were treated intravenously with either saline control or nanoparticle preparations prepared in Examples 1 and 2, at a dose of 10 mg/kg/day. Organs from each mouse were collected at 16 hours after nanoparticle administration and ground completely with the Beadbeater. The analyte drugs were extracted from the ground tissues with acetonitrile, and the drug concentrations in each tissue were analyzed by LC/MS. The drug concentrations delivered to each tissue relative to the Injected Dose (ID) were measured in both healthy and tumor tissues, as shown in Table 3.

TABLE 3

| | healthy % ID/g | tumor % ID/g |
|---|---|---|
| Free drug paclitaxel | 0.1~2.3 | 0.52 |
| Free drug doxorubicin | 0.4~3.4 | 1.5 |
| Free drug oxaliplatin | 0.1~3.5 | 2.5 |
| Free drug gemcitabine | 0.2~4.2 | 2.4 |
| Targeting-enhanced nanoparticles with paclitaxel (JINIS nanoparticles) | 0.1~2.4 | 8.1 |
| Targeting-enhanced nanoparticles with doxorubicin (JINIS nanoparticles) | 0.5~2.8 | 16.4 |
| Targeting-enhanced nanoparticles with oxaliplatin (JINIS nanoparticles) | 0.1~3.9 | 10.5 |
| Targeting-enhanced nanoparticles with gemcitabine (JINIS nanoparticles) | 0.2~2.5 | 12.7 |

As shown in Table 3, no significant differences in drug delivery were observed between the tumor tissue and healthy tissues for animals receiving free drug, as determined by free drug concentration. In contrast, drug delivery was significantly increased in the tumor tissue compared to the healthy tissues in animals treated with the targeting-enhanced nanoparticles prepared in Examples 1 and 2.

In this experiment, the drug delivery of the targeting-enhanced nanoparticles of paclitaxel prepared in Example 1 was also measured in each tissue in comparison with albumin-bound paclitaxel, Abraxane® (Celgene Co.).

This experiment further confirmed that the targeting-enhanced nanoparticles with paclitaxel prepared in Example 1 amplified tumor targeting. Targeting-enhanced nanoparticles containing paclitaxel were administered intravenously to mice with tumor xenografts, and at 4 hours after injection, the mice were exposed to a light-emitting diode, LED, at the wavelength of 630 nm at an intensity of 100 mmol/m²s² for 30 minutes.

Figure 5:
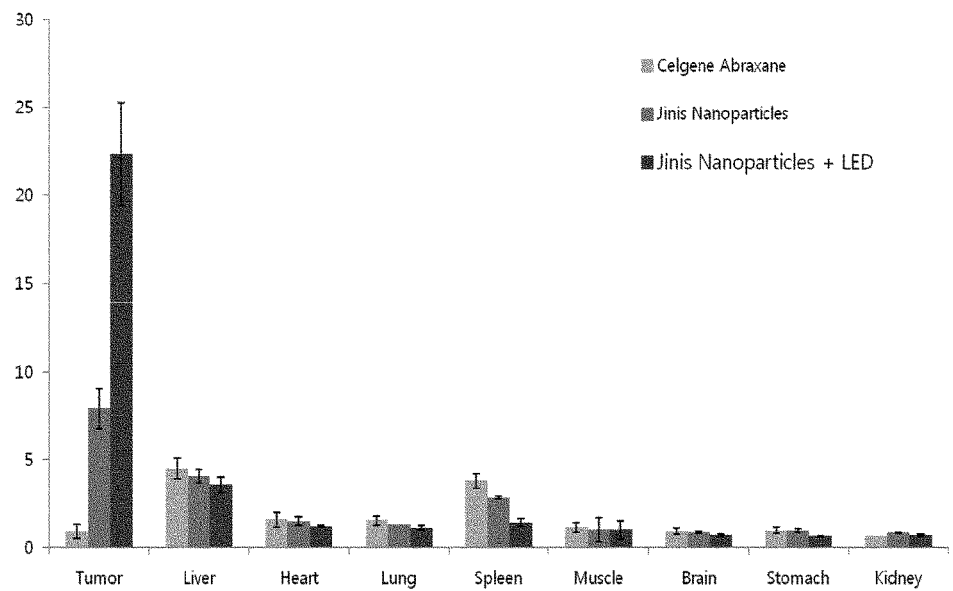
FIG. 5 is the drug concentration data in healthy and tumor tissues after the injection of targeting-enhanced anticancer nanoparticles prepared by the method in Example 1 (Grey bar: Abraxane® of Celgene, Dark grey bar: targeting-enhanced nanoparticles of paclitaxel, Black bar: targeting-enhanced nanoparticles of paclitaxel with LED).

As shown in FIG. 5, the drug delivery to the tumor tissue in the Abraxane® treatment group was not much different than that to the healthy tissue, indicating inefficient tumor targeting. In contrast, for the group receiving targeting-enhanced nanoparticles containing paclitaxel, the drug delivery to the tumor was 7-9% ID/gram compared with 0.1-2.4% ID/gram in the healthy tissues such as the liver, heart, lung, spleen, muscle, brain, stomach, and others, indicating significantly enhanced tumor targeting. In particular, the drug delivery to tumor tissues treated with LED irradiation was in the range of 19~26% ID/gram, indicating further enhanced tumor targeting.

Experiment 3: Toxicity of Targeting-Enhanced Nanoparticles

The toxicity of the targeting-enhanced nanoparticles formulated in Example 1 to healthy tissues was evaluated.

The breast cancer cell line MDA-MB-231 (KCLB®, Korean Cell Line Bank) was prepared as a cell suspension, and 5×10⁶ cells were injected subcutaneously into 6-8 week-old female athymic nude mice (Damool Science, Korea) under a specific pathogen-free environment to generate xenograft tumor growth of more than 200 mm³.

After establishment of the tumor-xenograft model, either healthy mice or tumor-xenografted mice were divided into three groups (n=6) receiving saline solution (control group), free paclitaxel at the indicated dose, or targeting-enhanced nanoparticles in saline solution at the indicated dose of paclitaxel. Free drug was administered to healthy mice at 7 different dosages: 20, 40, 60, 80, 100, 120, and 250 mg/kg/day. To evaluate their toxicity, targeting-enhanced nanoparticles were administered to healthy mice and tumor-xenograft mice at 10 different dosages of paclitaxel: 20, 40, 60, 80, 100, 120, 250, 300, 350, and 400 mg/kg/day. Body weights and physical changes were monitored over 14 days, and the LD50s were calculated based on mortality.

Figure 6A:
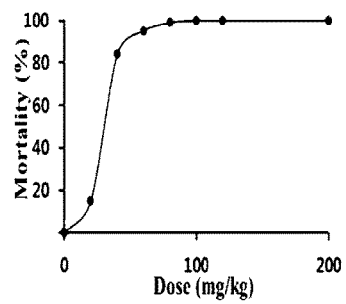
FIGS. 6A, 6B and 6C show the toxicity data of targeting-enhanced nanoparticles prepared by the methods in Example 1 and Experiment 3 (FIG. 6A: LD50 of the free drug paclitaxel in healthy mice, FIG. 6B: LD50 of targeting-enhanced nanoparticles containing paclitaxel in healthy mice, FIG. 6C: LD50 of targeting-enhanced nanoparticles containing paclitaxel in tumor-xenograft mice).
Figure 6B:
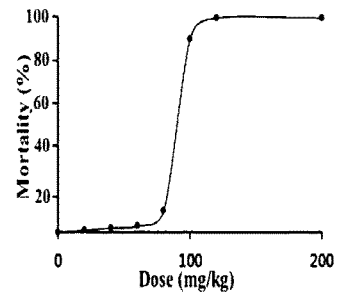
Figure 6C:
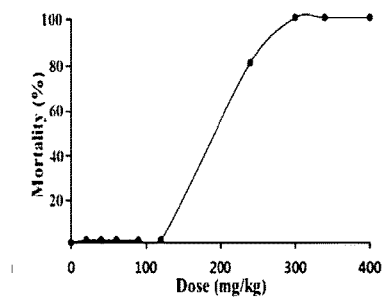

As shown in FIGS. 6A, 6B and 6C, the LD50 of the targeting-enhanced nanoparticles in healthy mice was significantly increased to 91 mg/kg/day, more than 3 times the LD50 of paclitaxel, 30 mg/kg/day.

The LD50 of the targeting-enhanced nanoparticles in tumor-xenograft mice further increased to 194 mg/kg/day (FIG. 6C), indicating that the enhanced tumor targeting and reduced delivery to healthy tissues significantly reduced the toxicity (see FIG. 5).

Experiment 4: EPR Enhancement of Targeting-Enhanced Nanoparticles

The key characteristics of targeting-enhanced nanoparticles prepared here are core-shell nanoparticles comprising non-covalently bound HSA and anticancer drugs with surface-exposed porphyrin compounds. Therefore, irradiation with electromagnetic waves after nanoparticle administration would be expected to enhance tumor targeting further through EPR, significantly increasing the preferential delivery of anticancer drugs to tumor tissues.

To confirm whether targeting-enhanced nanoparticles enhance the EPR effect, targeting-enhanced nanoparticles comprising HSA, porphyrin compounds, and paclitaxel prepared in Example 1 were injected into tumor-xenografted mice, and then the accumulation of Evans Blue Dye (SIGMA-ALDRICH) bound to HSA was observed in the tumors.

The lung cancer cell line NCI-H460 (KCLB®, Korean Cell Line Bank) was prepared in suspension and injected subcutaneously into female athymic nude mice to generate xenograft tumor growth of more than 50 mg in weight.

Tumor-xenografted mice were divided into three groups and received either saline solution for the control group, 20 mg/kg Abraxane® in saline, or 20 mg/kg of targeting-enhanced nanoparticles containing paclitaxel in saline solution.

Four hours after injection, the mice were exposed to an LED at a wavelength of 630 nm at an intensity of 100 mmol/m²s² for 30 minutes, followed by intravenous administration of 200 μL of Evans Blue Dye at 1 mg/mL. After 6 hours, the tumor tissue was removed from the mice and incubated in 3 ml of formamide in a 60° C. water bath for 48 hours. The Evans Blue Dye extracted from the tumor was quantitated by a spectrophotometer, as shown in FIGS. 7A and 7B.

Figure 7A:
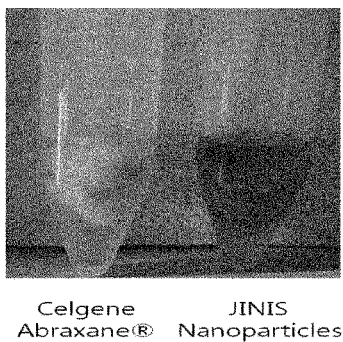
FIGS. 7A and 7B are a photograph (left) and absorption data (right) demonstrating that these targeting-enhanced nanoparticles containing paclitaxel exhibit the EPR effect, using the methods detailed in Example.
Figure 7B:
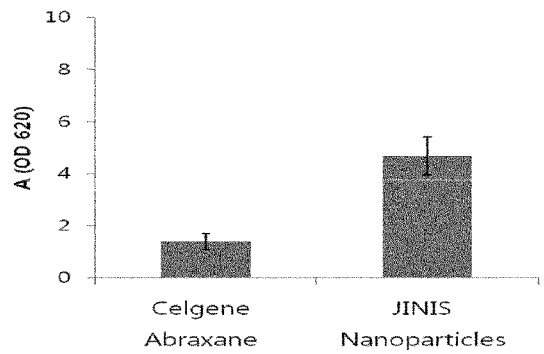

In FIGS. 7A and 7B, the targeting-enhanced nanoparticles containing paclitaxels, as prepared in Example 1, exhibited an enhanced EPR effect compared to that of the control and Abraxane® groups.

Experiment 5: Efficacy of Targeting-Enhanced Nanoparticles for Early-Stage Cancer The efficacy of targeting-enhanced nanoparticles prepared in Example 1 was evaluated by the method described below.

The breast cancer cell line MDA-MB-231 (KCLB®, Korean Cell Line Bank) was prepared in suspension, and 5×10⁶ cells were injected subcutaneously into 6- to 8-week old-female athymic Balb/C nude mice (Damool Science, Korea) and maintained until the tumor xenografts reached a size of 100 mm³ to generate an early-stage xenograft model.

After the breast tumor xenograft was established, mice received intravenous injections of saline control, 10 mg/kg of Abraxane® (Celgene Inc.) in saline, or 10 mg/kg of targeting-enhanced nanoparticles in saline at days 0, 3, 7, and 10 and were monitored for 3 weeks.

Tumor growth was monitored using bioluminescence imaging of luciferase-expressing cancer cell lines. Mice were injected intraperitoneally with D-luciferin at a dosage of 150 mg luciferin/kg body weight. Mice were then anesthetized under isoflurane gas supplemented with oxygen and placed under a camera equipped with a Xenogen IVIS 200 imager to generate a bioluminescent image using an IVIS imaging system (Xenogen). Bioluminescence color images were superimposed using Living Image software. Data were analyzed with Igor Pro imaging analysis software, as shown in FIG. 8.

Figure 8:
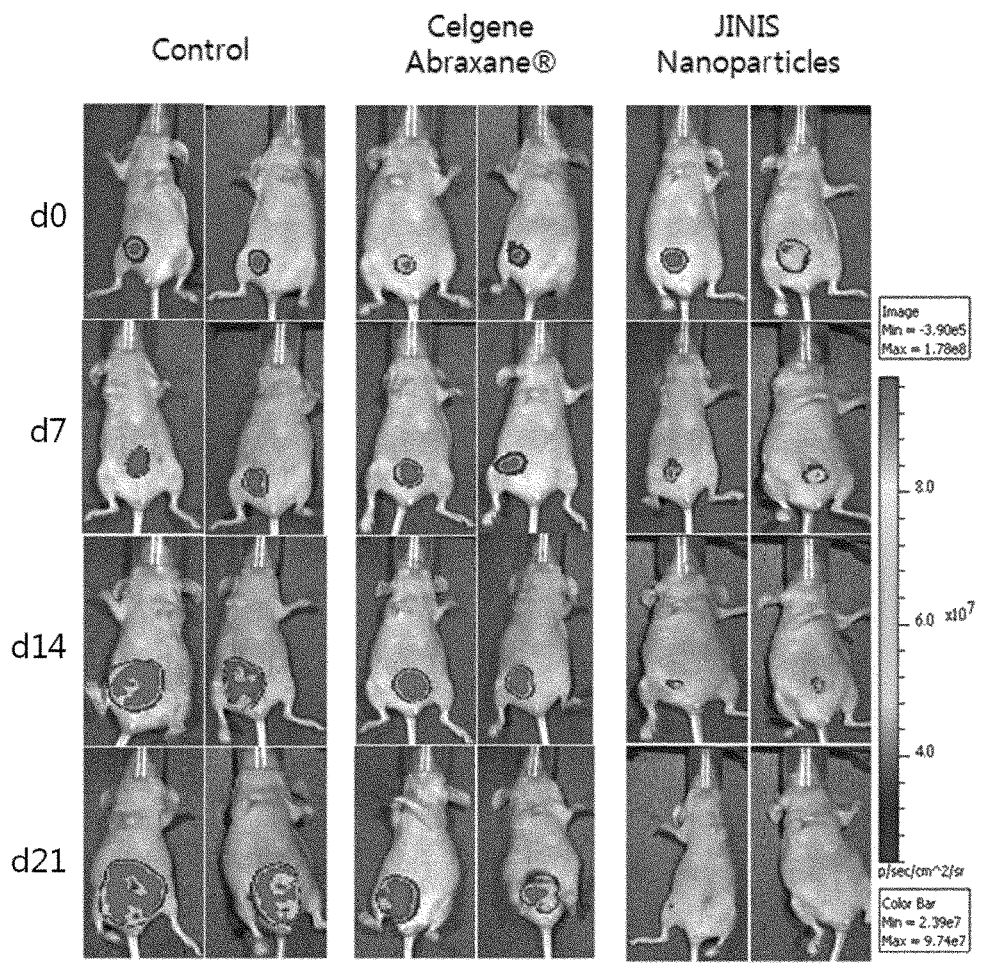
FIG. 8 shows images from mice with early-stage tumors demonstrating the anticancer efficacy of targeting-enhanced nanoparticles of paclitaxel using the methods described in Example 1.

In comparing the images in FIG. 8, the tumor size increased significantly from day 0 to day 21 in mice treated with saline, as expected. In Abraxane®-treated mice, clear tumor growth was observed at day 21, although the tumor size was smaller than that of the control. In contrast, the tumors completely disappeared in the group treated with the targeting-enhanced paclitaxel nanoparticles prepared in Example 1, thus demonstrating the incomparable efficacy of this carrier against tumor growth.

Experiment 6: Efficacy of Targeting-Enhanced Nanoparticles for Late-Stage Cancer The administration of targeting-enhanced anticancer nanoparticles followed by irradiation with electromagnetic waves could result in the amplification of tumor targeting and drug delivery via EPR, maximizing its possibility to cure cancer, even incurable large tumors typical of late-stage cancer. The efficacy of the targeting-enhanced nanoparticles prepared in Example 1 was evaluated with large tumor xenografts representing late-stage cancer as described below.

The lung cancer cell line NCI-H460-luc2 (Caliper Life Sciences) was prepared in suspension at $5 \times 10^6$ cells. The tumor cell suspension was injected subcutaneously into 6- to 8-week-old female athymic Balb/C nude mice (Damool Science, Korea) and maintained until the tumor xenografts reached a size of 500 mm³ to generate a late-stage xenograft model.

After establishing the lung tumor xenograft, mice subsequently received intravenous injections of saline control, Abraxane® (Celgene Inc.), or targeting-enhanced nanoparticles containing paclitaxel (JINIS nanoparticles) as prepared in Example 1, on days 0, 3, 7, 10, and 14. The paclitaxel dosage was 10 mg/kg/day for each drug injection. Mice was monitored for 4 weeks.

For the experimental group of amplification of tumor targeting, the tumor tissues of the mice were exposed to an LED at a wavelength of 630 nm at an intensity of 100 mmol/m²s² for 30 minutes following injection.

Tumor growth was monitored using bioluminescence imaging of luciferase-expressing cancer cell lines. Mice were injected intraperitoneally with D-luciferin at a dosage of 150 mg luciferin/kg body weight. Mice were then anesthetized under isoflurane gas supplemented with oxygen and placed under a camera equipped with a Xenogen IVIS 200 imager to generate a bioluminescent image using an IVIS imaging system (Xenogen). Bioluminescence color images were superimposed using Living Image software. Data were analyzed with Igor Pro imaging analysis software as shown in Table 4 and FIG. 9.

TABLE 4

|  | Day 0 tumor size (photons/sec) | Day 28 tumor size (photons/sec) |
|---|---|---|
| Saline control | 21.2E+08 | 120.4E+08 |
| Abraxane ® (Celgene) | 18.6E+08 | 87.3E+08 |
| Targeting-enhanced nanoparticles containing paclitaxel | 27.9E+08 | 0.8E+08* |

*E+08 is the value at background level for healthy tissues without tumors.

As shown in Table 4, comparing the tumor size between 0 and day 28 revealed significant tumor growth in the saline and Abraxane® groups. In contrast, the mice treated with targeting-enhanced nanoparticles containing paclitaxel, prepared as in Example 1, exhibited a huge decrease in tumor size after treatment, and the tumors were completely eradicated by day 28.

Figure 9:
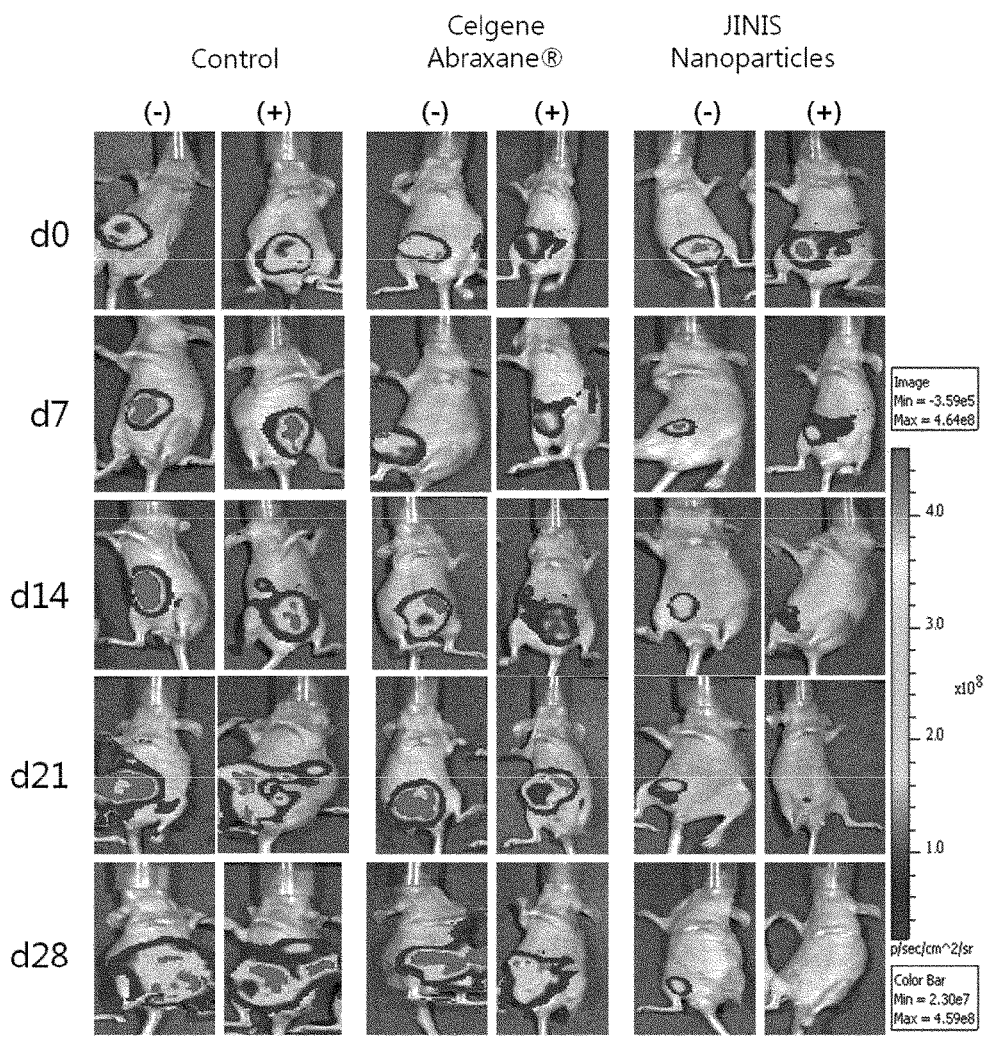
FIG. 9 shows images from mice with end-stage tumors demonstrating the anticancer efficacy of targeting-enhanced nanoparticles using the methods in Example 1.

FIG. 9 shows that the tumor size continued to increase in mice treated with saline. In Abraxane®-treated mice, clear tumor growth was also observed, although the tumor size was smaller than that of the control. In contrast, the tumors almost disappeared from mice treated with targeting-enhanced paclitaxel nanoparticles, thus demonstrating the incomparable efficacy of this carrier against tumor growth.

Irradiation with electromagnetic waves was also demonstrated to enhance the anticancer efficacy, as observed by comparing the LED (+) group to the group without irradiation, LED (−). In particular, the tumor was observed to completely disappear over days 21-28 in the mice treated with targeting-enhanced paclitaxel nanoparticles followed by treatment with electromagnetic waves.

Experiment 7: Efficacy of Targeting-Enhanced Nanoparticles Containing Doxorubicin for Late-Stage Cancer The efficacy of targeting-enhanced nanoparticles containing doxorubicin prepared in Example 2 was evaluated against large-sized tumor xenografts representing late-stage cancer, using the methods described in Experiment 6. These results are shown in FIG. 10.

Figure 10:
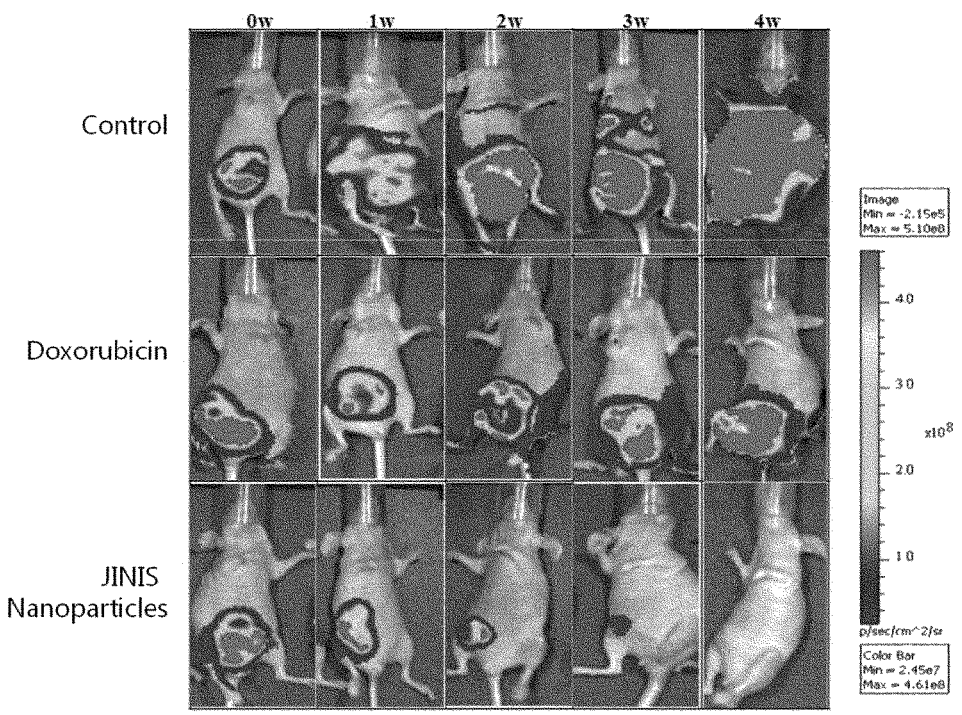
FIG. 10 shows the images from mice with late-stage tumors demonstrating the anticancer efficacy of targeting-enhanced nanoparticles of doxorubicin using the methods in Example 2.

FIG. 10 shows that the tumor size increased significantly from day 0 to day 28 in mice treated with saline. Mice treated with free doxorubicin also exhibited clear tumor growth, although the tumor size was smaller than that of the control.

In contrast, the tumors almost disappeared in mice treated with targeting-enhanced doxorubicin nanoparticles prepared in Example 2 followed by LED treatment, which demonstrates the incomparable efficacy of targeting-enhanced nanoparticles.

These data are in agreement with the results of Experiment 6 on the intravenous administration of targeting-enhanced nanoparticles containing paclitaxel followed by subsequent treatment with electromagnetic waves.

This full description of certain embodiments of the present invention will make other equivalent or alternative uses of these targeting-enhanced nanoparticles apparent to those skilled in the art. This invention has been described above by way of illustration, and the specific embodiments disclosed are not intended to limit the invention to the particular forms disclosed. The invention is thus to cover all modifications, equivalents, and alternatives falling within the spirit and scope of the following claims.

INDUSTRIAL USES

It remains difficult to achieve clinical cancer cures with current chemotherapeutic drugs. In particular, the clinical efficacies of current chemotherapeutic drugs and nanomedicines are extremely poor in late-stage cancer, with accelerated growth and increases in tumor volume preventing the clinical application of chemotherapy for late-stage cancer.

The targeting-enhanced nanoparticles in this invention have demonstrated outstanding anticancer efficacy by themselves, and further improved efficacy upon subsequent treatment with electromagnetic waves such as light or radiation, thereby amplifying the tumor targeting of the nanoparticles and enabling cures for late-stage cancer. Therefore, the targeting-enhanced nanoparticles in this invention have the potential to greatly improve clinicians' ability to control cancer.

The invention claimed is:

1. A preparation method for non-covalently bound targeting-enhanced nanoparticles, comprising
   (a) a preparation step of a mixture solution in which the anticancer drug solution is added to serum albumin solution;
   (b) a nanoparticle aggregate preparation step in which anticancer drugs and serum albumins aggregate upon the addition of organic solvents drop wise to the said mixture;
   (c) a manufacturing step in which drug-albumin nanoparticles are prepared with drugs in the core and serum albumin as the outer shell by inducing the spatial rearrangement of components through a temperature shift in these nanoparticle solutions with non-covalent aggregates of drugs and serum albumins;

(d) a manufacturing step to prepare targeting-enhanced anticancer nanoparticles in which non-covalently bound serum albumin-porphyrin complex encapsulates the anticancer drugs by adding the porphyrin compounds to the nanoparticle in which the anticancer drugs in the core and serum albumin in the outer shell are non-covalently bound and then mixing;

(e) a manufacturing step in which the targeting-enhanced nanoparticles were filtered and centrifuged and then the sedimented nanoparticles were recovered; and (f) a preparation step in which the targeting-enhanced nanoparticle powder was prepared by freeze-drying.

2. A method for preparing a targeting-enhanced anticancer nanoparticle according to claim 1, wherein said porphyrin compounds is at least one selected form the group consisting of protoporphyrin IX, heme, hemin, zinc protoporphyrin, magnesium protoporphyrin, hematoporphyrin, benzoporphyrin, metalloporphyrin, texaphyrins, chlorins, bacteriochlorins, pthalocyanine, napthalocyanine, and derivatives thereof.

3. A method for preparing targeting-enhanced anticancer nanoparticles according to claim 1, wherein said preparation method further comprises a targeting-enhanced nanoparticle wherein the ratio of albumins, anticancer drugs, and porphyrin compounds is 100:(10-300):(0.01-10) by weight.

4. A method for preparing targeting-enhanced anticancer nanoparticles according to claim 1, wherein said inducing the spatial rearrangement of components through a temperature shift is carried out by heating for hydrophobic drugs or by cooling for hydrophilic drugs.

5. A method for preparing targeting-enhanced anticancer nanoparticles according to claim 4, wherein said temperature shift is carried out by heating at 40° C.-60° C. or by cooling at −10° C.−−70° C.

6. A method for preparing targeting-enhanced anticancer nanoparticles according to claim 1, wherein said preparation includes an additional step of ultrasound treatment before filtration to separate randomly aggregated nanoparticles and to control the nanoparticle size.

7. A method for preparing targeting-enhanced anticancer nanoparticles according to claim 1, wherein said anticancer drugs is at least one selected from the group consisting of doxorubicin, daunorubicin, valrubicin, epirubicin, idarubicin, paclitaxel, docetaxel, cisplatin, carboplatin, oxaliplatin, camptothecin, vincristine, vinblastine, 5-FU, mitomycin, cyclophosphamide, methotrexate, mitoxantron, topotecan, capecitabine, doxifluridine, irinotecan, tegafur, chlorambucil, belotecan, anasterozole, tamoxifen, gleevec, floxuridine, leuprolide, flutamide, zoledronate, streptozocin, vinorelbine, hydroxyurea, retinoic acid, meclorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, and any combinations of the above or derivatives thereof.

* * * * *